(12) United States Patent
Weckstrom

(10) Patent No.: US 9,295,410 B2
(45) Date of Patent: Mar. 29, 2016

(54) AIRWAY ADAPTER AND GAS ANALYZER FOR MEASURING OXYGEN CONCENTRATION OF A RESPIRATORY GAS

(75) Inventor: Kurt Weckstrom, Helsinki (FI)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 907 days.

(21) Appl. No.: 13/468,386

(22) Filed: May 10, 2012

(65) Prior Publication Data

US 2012/0325214 A1 Dec. 27, 2012

(30) Foreign Application Priority Data

May 13, 2011 (EP) .................................. 11165954

(51) Int. Cl.
*A61M 16/00* (2006.01)
*G01J 1/58* (2006.01)
*A61B 5/087* (2006.01)
*G01F 1/32* (2006.01)
*A61B 5/083* (2006.01)

(52) U.S. Cl.
CPC .............. *A61B 5/087* (2013.01); *A61B 5/0833* (2013.01); *G01F 1/3218* (2013.01); *A61B 5/0836* (2013.01)

(58) Field of Classification Search
CPC ...... A61M 16/00; A61B 5/087; A61B 5/0833
USPC .................... 128/205.23; 422/82.08
See application file for complete search history.

(56) References Cited

U.S. PATENT DOCUMENTS

| 4,608,344 | A | | 8/1986 | Carter et al. |
|---|---|---|---|---|
| 4,683,760 | A | * | 8/1987 | Misumi ..................... 73/861.22 |
| RE33,064 | E | * | 9/1989 | Carter et al. .................... 436/34 |
| 5,088,332 | A | | 2/1992 | Merilainen et al. |
| 5,119,463 | A | * | 6/1992 | Vurek et al. ................... 385/129 |
| 5,178,018 | A | | 1/1993 | Gill |
| 6,312,389 | B1 | | 11/2001 | Kofoed et al. |
| 6,325,978 | B1 | | 12/2001 | Labuda et al. |

(Continued)

FOREIGN PATENT DOCUMENTS

| CN | 1281976 A | 1/2001 |
|---|---|---|
| CN | 101523197 A | 9/2009 |

(Continued)

OTHER PUBLICATIONS

Menz, "Vortex flowmeter with enhanced accuracy and reliability by means of sensor fusion and self-validation", Measurement, vol. 22, pp. 123-128, 1997.

(Continued)

*Primary Examiner* — Jill Warden
*Assistant Examiner* — Jacqueline Brazin
(74) *Attorney, Agent, or Firm* — GE Global Patent Operation; Marc A. Vivenzio

(57) ABSTRACT

An airway adapter comprising a flow channel configured to carry a respiratory gas, and a body comprising a surface at least partially coated with a luminophore that is excited by received radiation, wherein the luminophore emits luminescent radiation indicative of oxygen concentration of the respiratory gas when the luminophore is in contact with the respiratory gas, wherein the body comprises a transparent radiation path surrounded by the surface, the body being configured to guide at least one of the received radiation and the luminescent radiation emitted by the luminophore.

18 Claims, 2 Drawing Sheets

(56) References Cited

U.S. PATENT DOCUMENTS

| | | | |
|---|---|---|---|
| 6,351,999 | B1 | 3/2002 | Maul et al. |
| 6,632,402 | B2 * | 10/2003 | Blazewicz et al. .............. 422/84 |
| 7,335,164 | B2 * | 2/2008 | Mace et al. ................... 600/532 |
| 2007/0225612 | A1 | 9/2007 | Mace et al. |
| 2010/0036272 | A1 * | 2/2010 | Mace ..................... A61B 5/083 |
| | | | 600/531 |

FOREIGN PATENT DOCUMENTS

| | | |
|---|---|---|
| CN | 101600391 A | 12/2009 |
| WO | 2008022191 A2 | 2/2008 |

OTHER PUBLICATIONS

Kolle et al., "Fast optochemical sensor for continuous monitoring of oxygen in breath-gas analysis", Sensors and Actuators B vol. 38-39, pp. 141-149, 1997.

White, "Vortex Flowmeter" pp. 393-394 from book Fluid Mechanics, Fourth edition, McGraw Hill, 1999.

European Search Report and Written Opinion issued in connection with corresponding EP Application No. 11165954.6 dated Oct. 31, 2011.

Unofficial English Translation of Chinese Office Action and Search Report issued in connection with corresponding CN Application No. 201210234763.3 on May 4, 2015.

* cited by examiner

AIRWAY ADAPTER AND GAS ANALYZER FOR MEASURING OXYGEN CONCENTRATION OF A RESPIRATORY GAS

BACKGROUND OF THE INVENTION

1. Field of the Invention

Embodiments of the present invention relate generally to an airway adapter and a gas analyzer for measuring oxygen concentration of a respiratory gas.

2. Description of the Prior Art

In anesthesia or in intensive care, the condition of a patient is often monitored by analyzing the gas exhaled by the patient for its content. For this reason either a small portion of the respiratory gas is diverted to a gas analyzer or the gas analyzer is directly connected to the respiratory circuit. The former analyzer is known as a sidestream sensor, while the latter is known as a mainstream sensor because of its ability to measure directly across the respiratory tube. Typically, a mainstream sensor has a disposable airway adapter and a directly connectable sensor body. The majority of mainstream sensors on the market are designed to measure carbon dioxide alone, using an infrared non-dispersive (NDIR) absorption technique. As it is not directly related to this case, NDIR measurement will not be further described in this document.

Another gas of vital importance is, of course, oxygen. Oxygen can be measured using chemical sensors or fuel cells, but they are normally too bulky to fit into a mainstream sensor and, although they have a limited lifetime, they are not designed for a single use and must therefore be protected from direct contact with the patient gas to avoid contamination. This is expensive and also influences the response time of the sensor. Oxygen can also be measured using a laser at an absorption of 760 nm. However, this absorption is very weak and the signal from the short distance across the respiratory tube is too noisy to be useful. The most promising method is luminescence quenching. A special sensor coating, a luminophore, is excited using, for example, blue light from a light emitting diode (LED). A luminescence signal can be detected at longer wavelengths, often in the red portion of the spectrum. Oxygen has the ability to quench this luminescence in a predictable way by consuming the available energy directly from the luminophore. Thus, the amount of quenching is a direct measure of the partial pressure of oxygen in the respiratory gas mixture. Luminescence quenching offers the possibility to make a single use probe in connection with the patient adapter. However, problems associated with luminescence quenching relate to temperature and humidity dependence as well as drift caused by aging. Also, the luminescence intensity is not normally measured directly. Instead a change in the decay time of the excited state is a more stable and robust measurement. Still, an optical reference is normally a necessity, as is temperature compensation.

If carbon dioxide and oxygen can be measured reliably, it is possible to calculate oxygen consumption and carbon dioxide production of a patient, provided the respiratory flow is also known. The flow can be measured using a hot wire technique, but because of the difficult environment with water and mucus, it would require filtration of the respiratory gas. This again increases the flow resistance. A better method utilizes the pressure drop that develops across an obstacle in the gas stream or a pressure signal from a pitot tube. An interesting method is based on the behavior of vortexes formed downstream of a bluff body. The vortex flow meter has a large dynamic range and is fairly linear and robust. It can be based on vortex frequency estimation or vortex time of flight estimation. As will be evident below, the real advantage comes from the fact that the oxygen sensor can reside in the bluff body.

In the clinically used gas analyzer of a mainstream sensor, the whole volume, or at least the main portion of the breathing air or gas mixture, flows through the analyzer and its disposable measuring chamber. Because the measuring chamber is in the breathing circuit, it is easily contaminated by mucus or condensed water. Thus, it is necessary to use sensors that are as robust and insensitive to the conditions as possible. The infrared sensor uses one or more reference wavelengths in a mainstream analyzer in order to provide a good enough estimate of the signal level without gas absorption, the zero level, continuously available. For the oxygen sensor, it is important that contamination does not alter the sensitivity more than can be tolerated. The sensor based on luminescence quenching fulfills this demand. It is known that it works submerged in water as it measures the dissolved oxygen. The response time will naturally be longer in such a measurement. As already mentioned, the flow sensor must also tolerate contamination. In this respect the sensor based on vortex formation seems to be reliable.

A clinical mainstream gas analyzer must be small, light, accurate, robust and reliable. It is not possible to make a zeroing measurement using a reference gas during its normal operation. Yet, the analyzer must maintain its accuracy even if the measuring chamber is contaminated. Due to these requirements, mostly single gas mainstream analyzers for carbon dioxide ($CO_2$) have been commercially available. A compact $CO_2$ and $O_2$ gas analyzer with flow sensor of the mainstream type has been technically very challenging.

Another requirement is that the measurement be fast enough to measure the breathing curve. In practice, the rise time would have to be in the order of about 200 ins or even shorter. For $CO_2$, this is possible to arrange using well known infrared measuring technique. The luminescent $O_2$ sensor, however, must have a very thin layer of active material in order to react fast enough. This decreases the signal, and to compensate, the sensor surface must be increased. For a small mainstream sensor with a luminophore coated window for measuring light transmission, this may be a problem. Regarding the flow sensor, it can be arranged to be fast if the related sensors are fast, so the response time is not a problem technically.

BRIEF SUMMARY OF THE INVENTION

According to an embodiment of the present invention, there is provided an airway adapter. The airway adapter comprises a flow channel configured to carry a respiratory gas, and a body comprising a surface at least partially coated with a luminophore that is excited by received radiation, wherein the luminophore emits luminescent radiation indicative of oxygen concentration of the respiratory gas when the luminophore is in contact with the respiratory gas, wherein the body comprises a transparent radiation path surrounded by the surface, the body being configured to guide at least one of the received radiation and the luminescent radiation emitted by the luminophore.

According to another embodiment of the present invention, there is provided a gas analyzer for measuring oxygen concentration of a respiratory gas. The gas analyzer comprises an emitter configured to emit radiation, a body comprising a surface at least partially coated with a luminophore, that is excited by the radiation emitted by the emitter, and wherein the luminophore emits luminescent radiation indicative of oxygen concentration of the respiratory gas when the luminophore is in contact with the respiratory gas, a filter configured to transmit the luminescent radiation emitted by the luminophore, and a detector configured to receive the luminescent radiation transmitted by the filter, wherein the body comprises a transparent radiation path surrounded by the surface, the body being configured to guide at least one of the radiation emitted by the emitter and the luminescent radiation emitted by the luminophore.

BRIEF DESCRIPTION OF THE DRAWINGS

Embodiments of the present invention will be more apparent to those skilled in the art upon reading the following description with reference to the accompanying drawings, in which.

DETAILED DESCRIPTION OF THE INVENTION

The above-mentioned shortcomings, disadvantages and problems are addressed herein which will be understood by reading and understanding the following specification.

Specific embodiments are explained in the following detailed description making a reference to accompanying drawings. These detailed embodiments can naturally be modified and should not limit the scope of the invention as set forth in the claims.

Figure 1:
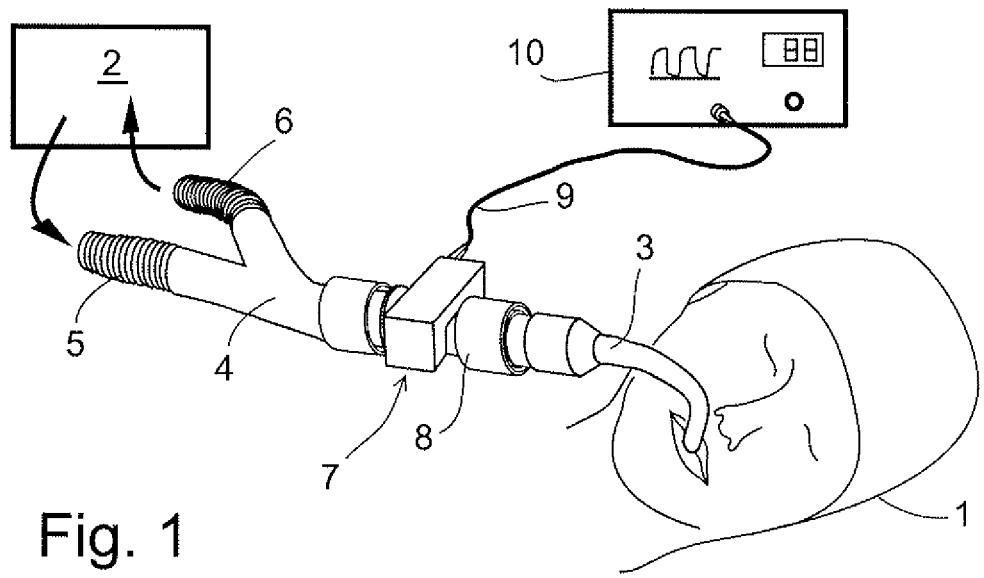
FIG. 1 illustrates a medical mainstream gas analyzer connected to the ventilation circuit of a patient.

A gas analyzer 7 for measuring a respiratory gas, such as oxygen, is described. Also an airway adapter 8 is described. Embodiments of the present invention may be applied in clinical multigas analyzers of mainstream type. Also, components of the gas analyzer 7 and the airway adapter 8 can be exploited when measuring a gas flow. The gas analyzer 7, such as a medical mainstream gas analyzer, may measure directly across the respiratory tube of an intubated patient 1 as shown in FIG. 1. The patient 1 may be connected to a ventilator 2 using an intubation tube 3, a Y-piece 4, an inspiratory limb 5 and an expiratory limb 6. The airway adapter 8 is connected to the intubation tube 3. The gas analyzer 7, which comprises components of the airway adapter 8, is electrically connected via cable 9 to a patient monitor 10. In addition to oxygen $O_2$, carbon dioxide $CO_2$, and other gases with infrared absorption such as nitrous oxide $N_2O$ and anesthetic gases, may be measured. Furthermore, respiratory gas flow and pressure for spirometry purposes can be measured. The spirometry sensor (not shown) may be separately connected, or may be integrated into the gas analyzer 7.

Figure 2:
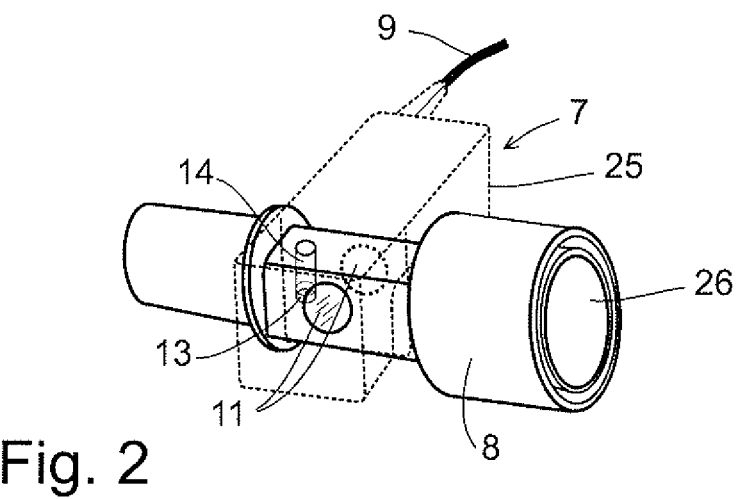
FIG. 2 shows an airway adapter and a gas analyzer according to an embodiment of the present invention.

In FIG. 2, a close-up of the gas analyzer 7 and the airway adapter 8 is depicted in order to better show the construction of an adapter 8, which normally may be disposable. The adapter 8 may be provided with two infrared transmitting windows 11 which are needed in case respiratory gases other than oxygen are measured. An infrared source (not shown) is located on one side of the adapter 8 and a non-dispersive filter assembly and detector(s) (not shown) on the opposite side. This configuration allows for the infrared radiation to be directed from the source through the windows 11 and respective narrowband filters to the detector or detectors. The signal from each detector is amplified and modified to reflect the concentration of the gas to be measured, or it may be a measurement at a reference wavelength with little or no gas absorption. As mentioned above, respiratory gases can be carbon dioxide, nitrous oxide and different volatile anesthetic agents. All these gases absorb infrared radiation within some specific wavelength region and this region may be selected using narrowband filters. The infrared non-dispersive (NDIR) gas measuring technique is well known and will not be further described here. Gases like oxygen that do not absorb enough infrared radiation using the short measuring channel between the windows 11, can be measured using a different principle based on luminescence quenching because of a number of additional benefits.

Oxygen sensors based on luminescence quenching in a mainstream adapter all include a window that transmits the radiation involved to and from a surface coated with a luminophore which can be excited by a radiation. According to embodiments of the present invention shown in FIGS. 2 and 3, an emitter 12 for emitting radiation is provided. The gas analyzer 7 comprises a body 14, such as an optical waveguide, having a surface 15 at least partly coated with the luminophore 13. The luminophore emits luminescent radiation indicative of oxygen concentration of the respiratory gas when the luminophore is in direct contact with the respiratory gas. The body 14, which may be rigid, comprises a transparent radiation path 20 surrounded by the surface 15. The airway adapter 8, having a flow channel 26 for carrying the respiratory gas including oxygen, may comprise only part of the components of the gas analyzer 7, such as the body 14 with the transparent radiation path 20 and the surface 15 at least partly coated with the luminophore 13. In this case, the adapter 8 can be made disposable. The airway adapter 8 may, if desired, also comprise the emitter 12, in which case it can be an integral part of the adapter 8. The emitter may also be a detachable component. In either case, the airway adapter 8 may be made without the emitter 12. The body 14, and thus the transparent radiation path 20, can be made of a transparent polymer, and is therefore inexpensive. It could also be made of glass or any other transparent solid material like ceramic. In one embodiment, the gas analyzer 7 further comprises a filter 18 for transmitting luminescent radiation emitted by the luminophore 13 and a detector 16 for receiving the luminescent radiation transmitted by the filter 18.

Figure 3:
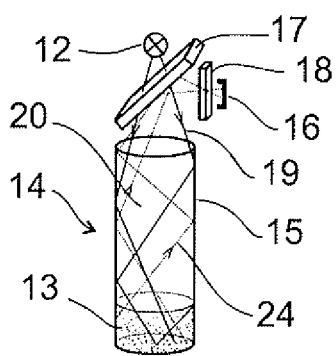
FIG. 3 shows an oxygen measuring principle and components of FIG. 2 according to an embodiment of the present invention.
Figure 4:
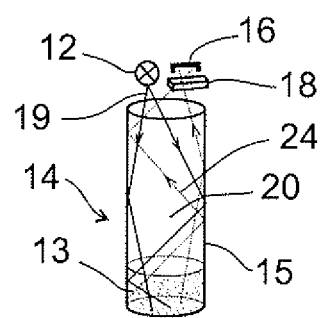
FIG. 4 shows an oxygen measuring principle and components of FIG. 2 according to an embodiment of the present invention.
Figure 5:
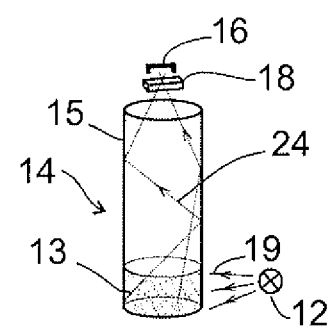
FIG. 5 shows an oxygen measuring principle and components of FIG. 2 according to an embodiment of the present invention.

The measuring principle of the gas analyzer 7 for measuring oxygen concentration is shown in FIGS. 3, 4 and 5. The emitter 12 for exciting the luminophore 13 and the detector 16 for detecting the luminescent radiation are located in a housing 25, which is part of the gas analyzer 7, and which may not be disposable. The housing 25 may be mountable on the airway adapter 8. Optically, the gas analyzer 7 can be assembled in a number of ways, three of which are shown. In FIG. 3 a dichroic beam splitter 17 is used to transmit the exciting radiation from the emitter 12, such as a light emitting diode (LED), and to reflect the luminescence radiation, such as the light emitted by the luminophore 13, to the detector 16. LEDs often emit in the blue region but, depending on the chemical composition of the luminophore, yellow light may also be used as exciting radiation. The emitter 12 may be equipped with an optical filter (not shown) to remove the possible infrared part of its emission. The filter 18 in front of the detector 16 is normally needed to filter out the radiation, including light wavelengths, from the emitter 12 and also to disturb ambient light, if such exists, transmitting only luminescence radiation, which normally has its maximum in the red end of the spectrum. In principle, it is possible to combine the filter 18 into the dichroic beam splitter 17. The assembly shown in FIG. 4 is simpler and allows for mounting of the electric parts, the emitter 12 and the detector 16, in the housing 25 of the gas analyzer 7.

In both cases shown in FIGS. 3 and 4, exciting radiation rays 19, such as light rays from the emitter 12, enter the body 14 made of transparent material through one end and are guided by total internal reflection down the body 14. At some instance, the radiation rays 19 will excite the luminophore 13. The consequently emitted luminescence is emitted in all directions and part of the luminescent radiation 24 will be trapped inside the body 14 and transferred to the detector 16. The rigid body 14 may even to some extent concentrate the luminescent radiation on the detector 16 and consequently increase the detected signal. Oxygen on the outside of the rigid body 14 will quench the luminescence and a signal related to the concentration of oxygen can be calculated and displayed, for instance, in the patient monitor 10. This is done using well-known principles and applying the Stern-Volmer relationship:

$$I_0/I = 1 + K \cdot C(O_2),$$

where $I_0$ is the luminescence intensity in absence of oxygen, I is the measured intensity at concentration $C(O_2)$ of oxygen. The constant K is the Stern-Volmar constant. This equation could also be written as:

$$\tau_0/\tau = 1 + K \cdot C(O_2),$$

where $\tau_0$ is the luminescence decay time in absence of oxygen and $\tau$ is the measured decay time at concentration $C(O_2)$ of oxygen. The method is well known and described in detail, for example, in the document Kolle, C. et al.: Fast optochemical sensor for continuous monitoring of oxygen in breath-gas analysis, Sensors and Actuators B 38-39 (1997) 141-149, which is incorporated herein by reference.

The rigid body 14 can be used in a different manner according to FIG. 5 which illustrates that it is not necessary to direct the exciting radiation rays 19 into the body 14. The emitter 12 can be located anywhere provided that it is able to efficiently excite the luminophore 13. Excitation can happen both from inside and outside of the body 14.

The body 14 can have many different shapes depending on its possible use as part of a flow sensor, but also because of different efficiencies of delivering the exciting radiation and collecting the luminescent radiation. A length of the body 14 may be longer than a diameter of a cross-section of the body 14 guiding the luminescent radiation along a longitudinal axis of the body towards the detector 16. In FIGS. 3-5, the rigid body 14 is cylindrical with deposition of the luminophore 13 at the end located in the gas stream. The surface of the body 14 comprises a side surface and an end surface and at least one of them is at least partially coated with the luminophore 13. However, coating of the exposed surface area with the luminophore 13 can be increased considerably, not only on the end surface but also on the side surface of the body 14. In principle, the whole surface 15 exposed to the gas stream, or just part of the rigid body 14 comprising the transparent radiation path 20, can be coated. Typically at least 10%, more specifically at least 30%, and even more specifically at least 50%, of the surface 15 surrounding the transparent radiation path 20 is coated with the luminophore 13. The area of the surface surrounding the transparent radiation path 20 coated with the luminophore 13 is at least about 10 mm$^2$, more specifically at least about 30 mm$^2$, and even more specifically at least about 100 mm$^2$.

Figure 6:
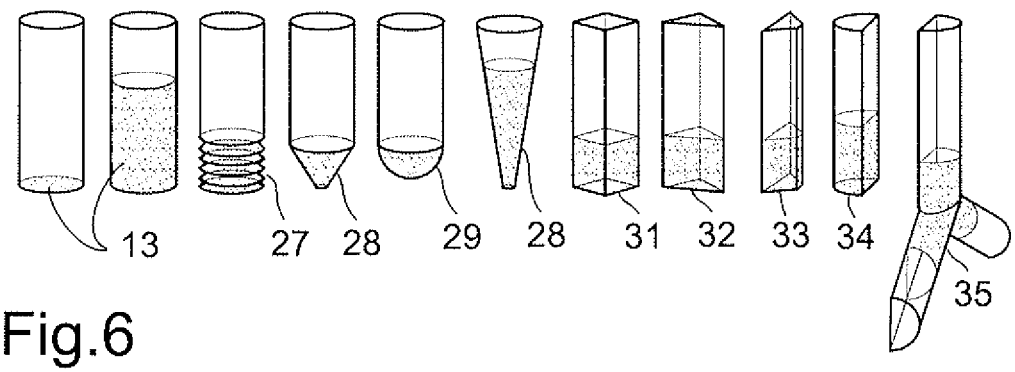
FIG. 6 shows different alternatives for bodies in FIGS. 3, 4 and 5 according to embodiments of the present invention.

The area coated with the luminophore 13, in addition to the end surface area, would then be the product of the circumference and the height of the coating. This is shown for the two first cylindrical rigid bodies 14 shown on the left in FIG. 6. The body 14 can have grooves 27 or it can be made mat to increase surface area and aid the escape of the exciting radiation 19 through the luminophore 13. The shape can be conical 28 or it can be a half-dome 29 in order to more efficiently collect luminescent radiation into the transparent radiation path 20 of the body 14. The body 14 does not have to be circular in cross-section. The body 14 can also have the shape of a square 31, a triangle 32, a trapezoid 33, a half circle 34 as is illustrated in the different embodiments as shown in FIG. 6. The body 14 could even have a completely different shape provided that the luminescent radiation can be collected. As an example, a tripartite construction 35 is shown as the last example on the right in FIG. 6. The benefit of such a shape could be in the flow sensor design.

Figure 7:
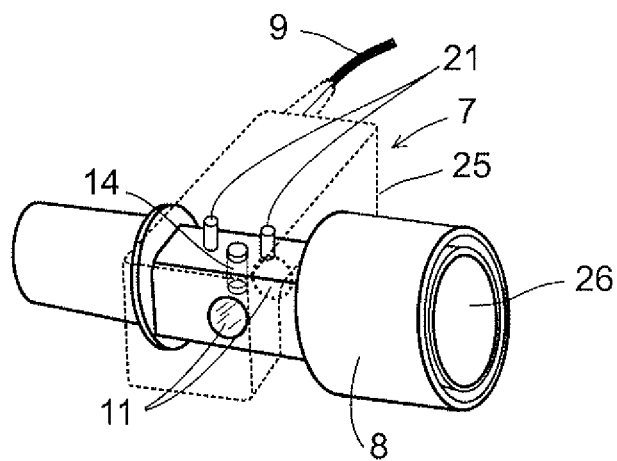
FIG. 7 shows an airway adapter of a gas analyzer according to an embodiment of the present invention.

When combining or integrating a flow sensor into the adapter 8 and the gas analyzer 7 as shown in FIG. 7, it is beneficial to make use of internal structures already available. This saves space and the adapter 8 can be made small with minimal dead space, which is a feature very important for neonatal use. The rigid body 14 for luminescent oxygen measurement is an obvious obstruction that changes the flow, but this change can be measured by a detector assembly 21. A differential pressure can be measured across the rigid body 14 and a signal indicative of the respiratory gas flow is provided by a detector assembly 21 which may comprise, for instance, two pressure ports connected to a differential pressure sensor. The detector assembly may be inside the housing 25 of the gas analyzer 7. If the rigid body 14 has a tripartite construction 35 like one of the embodiments shown in FIG. 6, it is similar to what is known in U.S. Pat. No. 5,088,332. The rigid body 14 may have to be symmetrical axially, in the flow direction, because the flow direction is altered depending on whether inspiratory or expiratory gas is being monitored. Another solution to this could also be to use two rigid bodies 14 with mirrored shapes. The assembly in FIG. 7 is made symmetrical by shifting the windows 11 for NDIR measurement to a position directly below the rigid body 14 so that the body 14 does not disturb the infrared measuring path 20. Thus it could be possible to connect the housing 25 to the airway adapter 8 either as shown or in such a way that cable 9 is in the opposite direction.

Another very useful method of measuring the respiratory gas flow, especially in this case, is a well-known method based on vortex formation. The rigid body 14 in FIG. 7 may serve as a bluff body for the flow measurement. Its diameter could be about 1-3 mm and its length could be from about half the diameter of the respiratory tube up to even the whole diameter. Downstream of the bluff body or, in this case the rigid body 14, flow dependent vortices will be formed. The vortex frequency is monitored by the detector assembly 21, which in this case can be, for example, piezoelectric pressure detectors and which pressure detectors can replace the pressure ports. The gas flow is essentially directly proportional to this frequency. For a bi-directional flow, the detector assembly 21 comprises two detectors.

Figure 8:
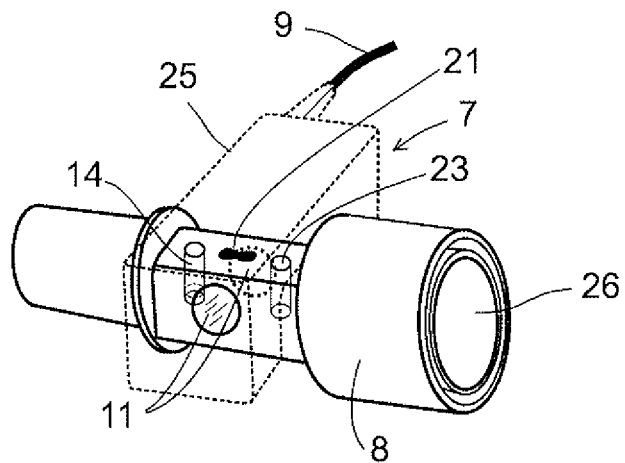
FIG. 8 shows an airway adapter of a gas analyzer according to an embodiment of the present invention.

According to an embodiment, the vortices can be measured by measuring their time of flight. The detector assembly 21, which may comprise two detectors spaced apart in the flow direction, can measure the time it takes for a vortex to move from one to the other. The detector assembly 21 can comprise a pressure sensor or, for example, a temperature sensor. For bi-directional flow, another similar mirrored bluff body 23 must be used as shown in FIG. 8. The time of flight method can be used together with the vortex frequency method to enhance the measuring range and accuracy as shown e.g. in Menz, B: Vortex flowmeter with enhanced accuracy and reliability by means of sensor fusion and self-validation, Measurement 22 (1997) 123-128, which is incorporated herein by reference. A vortex based flow meter is beneficial for respiratory measurements because it is essentially insensitive to humidity and gas composition unlike the method based on the pressure difference. The additional bluff body 23 can also be a rigid body comprising a transparent radiation path 20 and can be used as a reference to the gas analyzer 7 measuring oxygen concentration comprising the body 14 with the luminophore 13. It could, for example, be used to measure the temperature of the respiratory gas using luminescence or by incorporating a small thermistor. The temperature measurement could be located in the body 14, being closer to the temperature dependent luminophore 13. It could also make use of the detector assembly 21 provided that the detector is a temperature detector.

Compared to a gas analyzer with several discrete detectors, embodiments of the present invention save both money and space because fewer components are needed. When measuring the patient gas such as oxygen, especially in neonatal and pediatric cases, it is crucial that the solution is fast and lightweight and that it has a small volume to keep the dead space in the respiratory tubing acceptable, which is the case in embodiments of the present invention. An advantage of embodiments of the present invention is also that components used in the gas analyzer can be exploited when measuring the flow. Especially the structure for the flow measurement based on the vortex formation can be made compact, and incorporation of the structure used for the airway adapter 8 and the gas analyzer 7 based on luminescence quenching in one or more of its bluff bodies, can save space. Embodiments of the present invention also offer a relatively large oxygen sensor surface compared to the exposed volume as the bluff body is used as a rigid body for the exciting radiation and the luminescent radiation.

The written description uses examples to disclose the present invention, including the best mode, and also to enable any person skilled in the art to make and use the present invention. The patentable scope of the present invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A mainstream sensor comprising:
    an airway adapter comprising a flow channel configured to carry a respiratory gas; and
    a gas analyzer configured to measure oxygen concentration of the respiratory gas, the gas analyzer comprising a vortex flow meter, the vortex flow meter comprising a bluff body and a vortex flow meter detector assembly configured to measure a signal indicative of vortices formed downstream of the bluff body,
    wherein the bluff body comprises a surface at least partially coated with a luminophore that is excited by received radiation, wherein the luminophore emits luminescent radiation indicative of oxygen concentration of the respiratory gas when the luminophore is in contact with the respiratory gas, and
    wherein the bluff body further comprises a transparent radiation path surrounded by the surface, the bluff body being configured to guide at least one of the received radiation and the luminescent radiation emitted by the luminophore.

2. The mainstream sensor according to claim 1 further comprising an emitter configured to emit the received radiation, the emitter being one of an integral part of the airway adapter and a detachable component.

3. The mainstream sensor according to claim 1, wherein the surface is configured to transfer radiation by total internal reflection.

4. The mainstream sensor according to claim 1, wherein the transparent radiation path is an optical waveguide, wherein the optical waveguide is rigid and comprises the surface with or without the luminophore.

5. The mainstream sensor according to claim 1, wherein a length of the bluff body is longer than a diameter of a cross-section of the bluff body, wherein the luminescent radiation is guided along a longitudinal axis of the bluff body towards the detector configured to receive luminescent radiation.

6. The mainstream sensor according to claim 5, wherein the cross-section of the bluff body is one of circular, square, triangular, trapezoidal and half-circular.

7. The mainstream sensor according to claim 1, wherein the surface of the bluff body comprises a side surface and an end surface, wherein at least one of the side surface and the end surface is at least partially coated with the luminophore and that at least about 10% of the surface surrounding the transparent radiation path is coated with the luminophore.

8. The mainstream sensor according to claim 1, wherein an area of the surface surrounding the transparent radiation path coated with the luminophore is at least about 10 mm$^2$.

9. The mainstream sensor according to claim 1, wherein the bluff body is configured to obstruct the respiratory gas flow changing the flow which can be measured by a detector assembly configured to provide a signal indicative of the gas flow.

10. A gas analyzer for measuring oxygen concentration of a respiratory gas, the gas analyzer comprising:
    an emitter configured to emit radiation; and
    a vortex flow meter, the vortex flow meter comprising a bluff body and a vortex flow meter detector assembly configured to measure a signal indicative of vortices formed downstream of the bluff body,
    wherein the bluff body comprises a surface at least partially coated with a luminophore, that is excited by the radiation emitted by the emitter, and wherein the luminophore emits luminescent radiation indicative of oxygen concentration of the respiratory gas when the luminophore is in contact with the respiratory gas;
    a filter configured to transmit the luminescent radiation emitted by the luminophore; and
    a detector configured to receive the luminescent radiation transmitted by the filter,
    wherein the bluff body further comprises a transparent radiation path surrounded by the surface, the bluff body being configured to guide at least one of the radiation emitted by the emitter and the luminescent radiation emitted by the luminophore.

11. The gas analyzer according to claim 10, wherein the surface with or without the luminophore is configured to guide radiation by total internal reflection.

12. The gas analyzer according to claim 10, wherein the transparent radiation path is an optical waveguide, wherein the optical waveguide is rigid and comprises the surface with or without the luminophore.

13. The gas analyzer according to claim 12, wherein the optical waveguide is between the emitter and the surface with or without the luminophore.

14. The gas analyzer according to claim 10, wherein the emitter is configured to emit radiation in one of a blue region and a yellow region depending on a chemical composition of the luminophore.

15. The gas analyzer according to claim 10, wherein the filter is configured to filter out radiation from the emitter, to disturb ambient light, and to transmit only luminescent radiation.

16. The gas analyzer according to claim 10 further comprising an airway adapter comprising a flow channel configured to provide the respiratory gas flow to and from a patient.

17. The gas analyzer according to claim 16, wherein the bluff body is an integral part of the airway adapter, and wherein the bluff body extends from an edge of the flow channel towards a center of the flow channel to be in contact with the respiratory gas flow.

18. The gas analyzer according to claim 16 further comprising a housing configured to be mounted on the airway adapter, wherein the housing comprises the filter, the emitter, and the detector.

* * * * *